United States Patent [19]

D'Sidocky et al.

[11] Patent Number: 5,728,757

[45] Date of Patent: Mar. 17, 1998

[54] ZINC SALTS OF CITRACONAMIC ACID AND RUBBER COMPOUNDS CONTAINING SUCH SALTS

[75] Inventors: Richard Michael D'Sidocky, Ravenna; Lawson Gibson Wideman, Tallmadge; Bernard Matthew Bezilla, Jr., Stow; Cheng Shaw, Copley, all of Ohio

[73] Assignee: The Goodyear Tire & Rubber Company, Akron, Ohio

[21] Appl. No.: 695,051

[22] Filed: Aug. 9, 1996

[51] Int. Cl.$^6$ ..................................................... C08J 5/21
[52] U.S. Cl. ..................................................... 524/219
[58] Field of Search ............................................ 524/219

[56] References Cited

U.S. PATENT DOCUMENTS

| | | | |
|---|---|---|---|
| 4,433,114 | 2/1984 | Coran et al. | 525/332.6 |
| 5,194,513 | 3/1993 | Wideman et al. | 525/329.3 |
| 5,328,963 | 7/1994 | Muse et al. | 525/282 |

FOREIGN PATENT DOCUMENTS

| | | | |
|---|---|---|---|
| 0476310 | 8/1991 | European Pat. Off. | C08K 5/20 |
| 62-252763 | 11/1987 | Japan. | |
| 9207904 | 5/1992 | WIPO | C08K 5/3415 |
| 9309178 | 5/1993 | WIPO | C08L 7/00 |
| 9322377 | 11/1993 | WIPO | C08K 5/3415 |

*Primary Examiner*—Peter D. Mulcahy
*Attorney, Agent, or Firm*—Bruce J. Hendricks

[57] ABSTRACT

The present invention relates to a zinc salt of the formula:

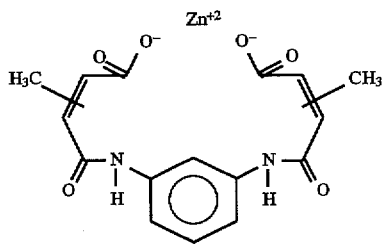

and rubber compounds containing such salts.

6 Claims, No Drawings

ZINC SALTS OF CITRACONAMIC ACID AND RUBBER COMPOUNDS CONTAINING SUCH SALTS

BACKGROUND OF THE INVENTION

PCT Application 93/0169 (International Publication No. WO 93/22377) discloses zinc salts of (poly)citraconimide and (poly)itaconimide. These zinc salts have use as antifatigue coagents for rubber vulcanization. The preparation of these compounds require a labor intensive and expensive dehydration step to form the imides.

SUMMARY OF THE INVENTION

The present invention relates to a zinc salt of the formula:

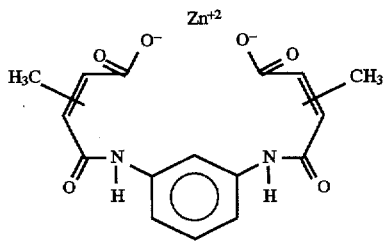

and rubber compounds containing such zinc salts.

DETAILED DESCRIPTION OF THE PREFERRED EMBODIMENT

The zinc salt of the present invention may be used at various levels in the rubber compounds of the present invention. For example, the level may range from about 0.1 to 10.0 by weight per 100 parts of rubber (also known as "phr"). Preferably, the level ranges from about 0.5 to about 5.0 phr.

The zinc salts of the present invention can be prepared by first condensing m-phenylene diamine with citraconamic anhydride to form N,N'-(m-phenylene)bis citraconamic acid. The acid is then reacted via a substitution reaction with sodium salt such as sodium hydrogen carbonate to form a soluble sodium salt which can be filtered free of impurities. The sodium salt is then reacted with a zinc salt such as $ZnCl_2$ to form the desired product. This method of preparation is preferred over standard zinc salt preparations utilizing zinc oxide or zinc acetate.

The citraconamic anhydride is reacted with the m-phenylenediamine under suitable conditions to form the N,N'-(m-phenylene)bis citraconamic acid. The anhydride may be reacted with the diamine compound in a variety of mole ratios. Generally, the mole ratio of the anhydride to the diamine compound ranges from about 2.5:1 to about 0.75:1 with a range of from about 2.1:1 to about 1.9:1 being preferred.

An organic solvent may be used to dissolve the anhydride or diamine compound. The solvent is preferably inert to the reaction between the anhydride and the diamine compound. Illustrative of solvents suitable for use in the practice of this invention include: saturated and aromatic hydrocarbons, e.g., hexane, octane, dodecane, naphtha, decalin, tetrahydronaphthalene, kerosene, mineral oil, cyclohexane, cycloheptane, alkyl cycloalkane, benzene, toluene, xylene, alkyl-naphthalene, and the like; acetone; ethers such as tetrahydrofuran, tetrahydropyran, diethylether, 1,2-dimethoxybenzene, 1,2-diethoxybenzene, the mono- and dialkylethers of ethylene glycol, propylene glycol, butylene glycol, diethylene glycol, dipropylene glycol, oxyethyleneoxypropylene glycol, and the like; fluorinated hydrocarbons that are inert under the reaction conditions such as perfluoroethane, monofluorobenzene, and the like. Another class of solvents are sulfones such as dimethylsulfone, diethylsulfone, diphenolsulfone, sulfolane, and the like. Mixtures of the aforementioned solvents may be employed so long as they are compatible with each other under the conditions of the reaction and will adequately dissolve the diamine or anhydride compound and not interfere with the reaction.

The reaction between the anhydride and the diamine compound to form the N,N'-(m-phenylene)bis citraconamic acid may be conducted over a wide temperature range. The temperature may range from moderate to an elevated temperature. In general, the reaction may be conducted at a temperature of between about 20° C. to 100° C. The preferred temperature range is from about 30° C. to 80° C., while the most preferred temperature range is from about 55° to 65° C.

The reaction to form the N,N'-(m-phenylene)bis citraconamic acid may be conducted under a variety of pressures. Pressures ranging from about 0 psig to 100 psig may be used.

The reaction between the N,N'-(m-phenylene)bis citraconamic acid and sodium hydrogen carbonate is generally carried out in an aqueous solution. Alternatives to sodium hydrogen carbonate include potassium or lithium hydrogen carbonate.

The N,N'-(m-phenylene)bis citraconamic acid is reacted with the sodium salt, such as sodium hydrogen carbonate, under suitable conditions to form the sodium salt of citraconamic acid. Representative sodium salts include sodium hydrogen carbonate, sodium ethoxide and sodium hydroxide. The bis citraconamic acid may be reacted with the sodium compound in a variety of mole ratios. Generally, the mole ratio of the acid to the sodium compound ranges from about 2.5:1 to about 0.75:1 with a range of from about 2.1:1 to about 1.9:1 being preferred.

The reaction between the acid and the sodium salt to form the sodium salt of the acid may be conducted over a wide temperature range. The temperature may range from moderate to an elevated temperature. In general, the reaction may be conducted at a temperature of between about 20° C. to 100° C. The preferred temperature range is from about 25° C. to 40° C., while the most preferred temperature range is from about 30° to 35° C.

The reaction to form the sodium salt of the acid may be conducted under a variety of pressures. Pressures ranging from about 0 psig to 100 psig may be used.

After the sodium salt is formed, it is reacted with a zinc salt to form the zinc salt of the acid. Representative zinc salts which may be used include zinc chloride and zinc bromide.

The mole ratio of the zinc salt to the sodium salt of the acid ranges from about 1.5:1 to 0.75:1, with a range of from 1.1:1 to 0.9:1 being preferred.

The process for the preparation of the zinc salt of citraconamic acid may be carried out in a batch, semi-continuous or continuous manner. The reaction may be conducted in a single reaction zone or in a plurality or reaction zones, in series or in parallel. The reaction may be conducted intermittently or continuously in an elongated tubular zone or in a series of such zones. The material of construction of the equipment should be such as to be inert during the reaction. The equipment should also be able to withstand the reaction temperatures and pressures. The reaction zone can be fitted with internal and/or external heat exchangers to control temperature fluctuations. Preferably, an agitation means is available to ensure the uniform reaction. Mixing induced by vibration, shaker, stirrer, rotating, oscillation, etc. are all illustrative of the types of agitation means which are contemplated for use in preparing the composition of the present invention. Such agitation means are available and well known to those skilled in the art.

The use of the zinc salt improves the anti-fatigue properties of "sulfur-vulcanized elastomers or rubbers." The term "sulfur-vulcanized elastomer or rubber" as used herein embraces both vulcanized forms of natural and all its various raw and reclaim forms as well as various synthetic rubbers. The synthetic elastomers include conjugated diene homopolymers and copolymers and copolymers of at least one conjugated diene and aromatic vinyl compound. Representative synthetic polymers include the homopolymerization products of butadiene and its homologues and derivatives, as for example, methyl-butadiene, dimethylbutadiene and pentadiene as well as copolymers, such as those formed from butadiene or its homologues or derivatives with other unsaturated organic compounds. Among the latter are acetylenes, for example, vinyl acetylene; olefins, for example, isobutylene, which copolymerizes with isoprene to form butyl rubber; vinyl compounds, for example, acrylic acid, acrylonitrile (which polymerizes with butadiene to form NBR), methacrylic acid and styrene, the latter polymerizing with butadiene to form SBR, as well as vinyl esters and various unsaturated aldehydes, ketones and ethers, e.g. acrolein, methyl isopropenyl ketone and vinylethyl ether. Also included are the various synthetic rubbers prepared by the homopolymerization of isoprene and the copolymerization of isoprene and other diolefins in various unsaturated organic compounds. Also included are the synthetic rubbers such as 1,4-cis-polybutadiene and 1,4-cispolyisoprene and similar synthetic rubbers.

Specific examples of synthetic rubbers include neoprene (polychloroprene), polybutadiene (including trans- and cis-1,4-polybutadiene), polyisoprene (including cis-1,4-polyisoprene), butyl rubber, copolymers of 1,3-butadiene or isoprene with monomers such as styrene, acrylonitrile and methyl methacrylate as well as ethylene/propylene terpolymers, also known as ethylene/propylene/diene monomer (EPDM) and, in particular, ethylene/propylene/dicyclopentadiene terpolymers and styrene/isoprene/butadiene rubber. The preferred synthetic rubbers for use in the present invention are polybutadiene, polyisobutylene, butadiene-styrene copolymers and cis, 1,4-polyisoprene.

Vulcanization of the rubber compound of the present invention is generally carried out at conventional temperatures ranging from about 100° C. to 200° C. Preferably, the vulcanization is conducted at temperatures ranging from about 110° C. to 180° C. Any of the usual vulcanization processes may be used such as heating in a press or mold, heating with superheated steam or hot air or in a salt bath.

In addition to the zinc salt of citraconamic acid, other rubber additives may also be incorporated in the rubber compound. The additives commonly used in rubber vulcanizates are, for example, carbon black, tackifier resins, processing aids, antioxidants, antiozonants, stearic acid, activators, waxes, phenol-formaldehyde resins, oils and peptizing agents. As known to those skilled in the art, depending on the intended use of the rubber compound, certain additives mentioned above are commonly used in conventional amounts. Typical additions of carbon black comprise about 20 to 100 parts by weight of diene rubber (phr), preferably 30 to 80 phr. Typical amounts of tackifier resins comprise about 1 to 5 phr. Typical amounts of antioxidants comprise 1 to about 10 phr. Typical amounts of antiozonants comprise 1 to about 10 phr. Typical amounts of stearic acid comprise 1 to about 2 phr. Typical amounts of zinc oxide comprise 2 to 5 phr. Typical amounts of waxes comprise 1 to 5 phr. Typical amounts of phenol-formaldehyde resins comprise 1 to 8 phr. Typical amounts of oils comprise 5 to 40 phr. Typical amounts of peptizers comprise 0.1 to 1 phr. The presence and relative amounts of the above additives are not an aspect of the present invention.

The vulcanization of the rubber compound is conducted in the presence of a sulfur-vulcanizing agent. Examples of suitable sulfur-vulcanizing agents include elemental sulfur (free sulfur) or sulfur donating vulcanizing agents, for example, an amine disulfide, polymeric polysulfide or sulfur olefin adducts. Preferably, the sulfur-vulcanizing agent is elemental sulfur. As known to those skilled in the art, sulfur-vulcanizing agents are used in an amount ranging from about 0.5 to 8 phr with a range of from 1.0 to 2.25 being preferred.

Accelerators are conventionally used to control the time and/or temperature required for vulcanization and to improve the properties of the vulcanizate. In some instances, a single accelerator system may be used, i.e., primary accelerator. Conventionally, a primary accelerator is used in amounts ranging from about 0.5 to 2.0 phr. In another instance, combinations of two or more accelerators may be used which may consist of a primary accelerator which is generally used in the large amount (0.5 to 2.0 phr), and a secondary accelerator which is generally used in smaller amounts (0.01–0.50 phr) in order to activate and to improve the properties of the vulcanizate. Combinations of these accelerators have been known to produce a synergistic effect of the final properties and are somewhat better than those produced by use of either accelerator alone. In addition, delayed action accelerators may be used which are not affected by normal processing temperatures but produce satisfactory cures at ordinary vulcanization temperatures. Suitable types of accelerators that may be used include amines, disulfides, guanidines, thioureas, thiazoles, thiurams, sulfenamides, dithiocarbamates and xanthates. Preferably, the primary accelerator is a sulfenamide. If a secondary accelerator is used, the secondary accelerator is preferably a guanidine, dithiocarbamate or thiuram compound.

The rubber compounds containing the zinc salts of the present invention may be used in the preparation of composite products including tires, power belts, conveyor belts, printing rolls, rubber shoe heels and soles, rubber wringers, automobile floor mats, mud flaps for trucks, ball mill liners, and the like. Preferably, the rubber vulcanizates are used in sidewall, carcass ply or overlay compounds for tires.

The following examples are presented in order to illustrate but not limit the present invention.

EXAMPLE 1

Preparation of Zinc N,N'-(m-phenylene)bis citraconamate

A 3-liter, 3-neck round bottom flask was charged with 54 g (0.5 mole) of m-phenylenediamine and 500 ml of reagent acetone and flushed with nitrogen. The flask was fitted with a reflux condenser, mechanical stirrer and thermocouple. A dropping funnel containing 112 g (1.0 mole) of citraconic anhydride in 500 ml of reagent acetone was attached and the solution added dropwise over about 1 ½ hours with stirring as the temperature was allowed to rise to reflux the acetone. The reaction mixture was refluxed for an additional hour, cooled to room temperature and suction filtered to give 166 g of N,N'-(m-phenylene)bis citraconamic acid as shown by NMR analysis, as a tan mustard-colored solid melting at 152°–156° C.

A 4-liter beaker was charged with 147 g (0.45 mole) of this bis citraconamic acid in about 5 g portions to a solution of 74.4 g (0.89 mole) of sodium hydrogen carbonate in 1500 ml of distilled water with stirring. After the evaluation of $CO_2$ gas and a solution is obtained, a freshly prepared solution of 61.2 g (0.45 mole) of $ZnCl_2$ in about 300 ml of distilled water is added as quickly as possible with vigorous agitation. A thick white precipitate immediately forms and is allowed to stand for about 15 minutes, suction filtered and air-dried to give 210 g of the white zinc salt melting at 192° C. and giving a zinc analysis of 12.9 percent.

EXAMPLE 3

Physical Testing

Table I below shows the basic rubber compound that was used in this example. Rubber stocks were prepared in order to compare the effects of using zinc N,N'-(m-phenylene) biscitraconamate versus a control compound not containing zinc N,N'-(m-phenylene)biscitraconamate. Zinc N,N'-(m-phenylene)biscitraconamate was compounded using conventional techniques and the samples vulcanized by compression molding methods for 36 minutes at 150° C.

The rubber compound was prepared in a two-stage Banbury mix. All parts and percentages are by weight unless otherwise noted. The cure data as well as other physical data for each sample are listed in Table II.

Cure properties were determined using a Monsanto oscillating disc rheometer which was operated at a temperature of 150° C. and at a frequency of 11 hertz. A description of oscillating disc rheometers can be found in the Vanderbilt Rubber Handbook edited by Robert O. Ohm (Norwalk, Conn., R. T. Vanderbilt Company, Inc., 1990), pages 554–557. The use of this cure meter and standardized values read from the curve are specified in ASTM D-2084. A typical cure curve obtained on an oscillating disc rheometer is shown on page 555 of the 1990 edition of the Vanderbilt Rubber Handbook.

In such an oscillating disc rheometer, compounded rubber samples are subjected to an oscillating shearing action of constant amplitude. The torque of the oscillating disc embedded in the stock that is being tested that is required to oscillate the rotor at the vulcanization temperature is measured. The values obtained using this cure test are very significant since changes in the rubber or the compounding recipe are very readily detected.

The following Table II reports cure properties that were determined from cure curves that were obtained for the two rubber formulations that were prepared. These properties include a torque minimum (Min Torque, $M_L$), minutes to 1 point of the torque increase (t1), minutes to 25 percent of the torque increase (t25 minutes) and minutes to 90 percent of the torque increase (t90 minutes).

Shore Hardness was determined in accordance with ASTM-1415.

The micron eye cut growth/fatigue measurement of compounds in this application was based on a computer control, fully automated cut growth test machine which was built based on the U.S. Pat. No. 4,911,017. A sample with a cut is mounted by clamps between a stationary bar and a movable bar causing the samples to undergo cyclic deformation at a suitable deformation range. A camera is selectively positioned to view each of the plurality of samples. A computer control determines a cut length from each two dimensional electronic video image representation and stores it in a cut data memory. The cut growth/fatigue resistance of rubber compounds were thus compared with cut length versus number of cycles plots.

As Table II illustrates, Control Sample 1 and Sample 2 were cured to give comparable physical properties so that a direct comparison could be made between Control Sample 1 and Sample 2 containing 1.0 phr of zinc N,N'-(m-phenylene) biscitraconamate. The data shows the flex improvement zinc N,N'(m-phenylene)biscitraconamate provided versus the control sample. Whereas Control Sample 1 showed onset of cut growth behavior at 2,400,000 cycles, Sample 2 containing zinc N,N'-(m-phenylene)biscitraconamate showed no cut growth behavior after 3,800,000 cycles. These examples demonstrate the anti-fatigue properties of zinc N,N'-(m-phenylene)biscitraconamate.

Additional compound was mixed in order to evaluate the anti-fatigue properties of zinc N,N'-(m-phenylene) biscitraconamate using the Monsanto Fatigue to Failure test procedure described by ASTMD 4482. Details on cure and physical properties are given in Table II referenced as Control Sample 3 and Sample 4. As Table II illustrates, Control Sample 3 and Sample 4 were cured to give comparable physical properties so that a direct comparison could be made between Control Sample 3 and Sample 4 containing 1.0 phr of zinc N,N'-(m-phenylene)biscitraconamate. The data shows the flex improvement zinc N,N'-(m-phenylene) biscitraconamate provided versus the control. Control Sample 3 and Sample 4 were aged 5 days at 120° C. in nitrogen to evaluate the potential to extend fatigue properties with age. As the data illustrates, whereas Control Sample 3 failed after 147 Kcycles, Sample 4 containing zinc N,N'-(m-phenylene)biscitraconamate failed after 700 Kcycles. This represents a significant improvement over Control Sample 3. These examples thus again demonstrate the improvement in anti-fatigue properties provided by zinc N,N'-(m-phenylene)biscitraconamate.

TABLE I

|  | Control Sample 1 | Sample 2 | Control Sample 3 | Sample 4 |
| --- | --- | --- | --- | --- |
| Non-Productive | | | | |
| Natural Rubber | 40.0 | 40.0 | 40.0 | 40.0 |
| Polybutadiene | 60.0 | 60.0 | 60.0 | 60.0 |
| Carbon Black | 51.0 | 51.0 | 51.0 | 51.0 |
| Zn Salt of Example 1 | 0 | 1.0 | 0 | 1.0 |
| Phenol formaldehyde resin | 5.0 | 5.0 | 5.0 | 5.0 |
| Fatty Acid | 1.0 | 1.0 | 1.0 | 1.0 |
| Processing Oils | 11.0 | 11.0 | 11.0 | 11.0 |
| Waxes | 1.0 | 1.0 | 1.0 | 1.0 |
| Productive | | | | |
| Zinc Oxide | 3.50 | 3.50 | 3.5 | 3.5 |
| Insoluble Sulfur | 2.81 | 2.81 | 2.81 | 2.81 |
| Accelerator | .50 | .50 | .50 | .50 |

TABLE II

| | Control Sample 1 | Sample 2 | Control Sample 3 | Sample 4 |
|---|---|---|---|---|
| Monsanto Fatigue to Failure[1] (Cure 36 min/150° C.) Aging (None) | | | | |
| CAM NUMBER 18 (119% extension) Kcycles to failure | | | 1186 | 1212 |
| Aging = 5 DAYS NITROGEN @ 120° C. Kcycles to failure | | | 147 | 700 |
| Micron Eye Cut Growth[2] (cured 36 min @ 150° C.) | | | | |
| Cycles to Cut Growth Initiation | 2,400,000 | >3,800,000 | | |
| Rheometer @ 150° C. | | | | |
| $M_{HF}$ Torque Units[3] (dNm) | 29.4 | 29.6 | 29.8 | 31.7 |
| $M_L$ Torque Units[4] (dNm) | 8.1 | 6.5 | 7.6 | 7.5 |
| $M_{HF}$-$M_L$ Torque Units (dNm) | 21.3 | 23.1 | 22.2 | 24.2 |
| Time to 1 PT Rise, min | 6.4 | 5.7 | 6.7 | 6.5 |
| Cure Time, t'c(25), min | 11.7 | 11.8 | 12.2 | 13.2 |
| Cure Time, t'c(90), min | 36.7 | 42.0 | 41.0 | 58.0 |
| Stress-Strain Data (cured 36 min @ 150° C.) | | | | |
| Modulus at 300% Elongation, MPa | 5.75 | 6.29 | 5.61 | 5.72 |
| Tensile Strength, MPa | 13.63 | 13.38 | 13.51 | 13.51 |
| Elongation at Break, % | 647 | 590 | 644 | 635 |
| Hardness | | | | |
| Shore A Hardness at room temp | 50.3 | 50.9 | 50.8 | 51.1 |
| Shore A Hardness at 100° C. | 47.8 | 48.4 | 47.4 | 47.4 |
| Rebound | | | | |
| Percent Rebound at room temp | 54.8 | 55.0 | 54.2 | 54.6 |
| Percent Rebound at 100° C. | 61.9 | 61.2 | 59.3 | 59.7 |

[1]ASTM Designation D4482
[2]Described in U.S. Pat. No. 4,911,017
[3]Maximum torque where curve plateaus are in dNm
[4]Minimum torque in dNm

What is claimed is:

1. A vulcanized rubber composition comprising a sulfur-vulcanized rubber and from 0.1 to 10 phr of a zinc salt of the formula:

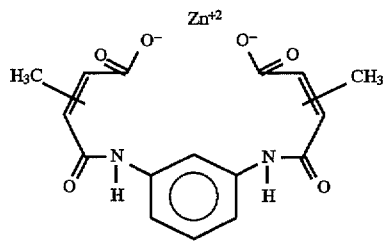

2. The rubber composition of claim 1 wherein said rubber is selected from the group consisting of a natural rubber and synthetic elastomeric selected from conjugated diene homopolymers and copolymers and from copolymers of at least one conjugated diene and aromatic vinyl compound.

3. The rubber composition of claim 2 wherein said rubber is selected from the group consisting of natural rubber, polychloroprene, synthetic 1,4-cis-polyisoprene, butyl rubber, polybutadiene, styrene-butadiene copolymer, isoprene-butadiene copolymer, styrene-isoprene-butadiene rubber, methyl methacrylate-butadiene copolymer, isoprene-butadiene copolymer, methyl methacrylate-isoprene copolymer, acrylonitrile-isoprene copolymer, acrylonitrile-butadiene copolymer, EPDM and mixtures thereof.

4. The rubber composition of claim 1 wherein said composition is used in a product selected from the group consisting of tires, power belts, conveyor belts, rubber wringers, automobile floor mats, mud flaps and ball mill liners.

5. The rubber composition of claim 4 wherein said product is a tire.

6. The rubber composition of claim 5 wherein said composition is used in a component of a tire selected from the group consisting of a sidewall, carcass ply and overlay compound.

* * * * *